United States Patent [19]

Ryan et al.

[11] Patent Number: 5,990,359

[45] Date of Patent: Nov. 23, 1999

[54] PROCESS FOR THE PRODUCTION OF FLUOROMETHYLHEXAFLUORO-ISOPROPYLETHER

[75] Inventors: Thomas Anthony Ryan, Kelsall; Leslie Burgess, Runcorn, both of United Kingdom

[73] Assignee: Imperial Chemical Industries PLC, United Kingdom

[21] Appl. No.: 09/101,125

[22] PCT Filed: Dec. 6, 1996

[86] PCT No.: PCT/GB96/03001

§ 371 Date: Jun. 30, 1998

§ 102(e) Date: Jun. 30, 1998

[87] PCT Pub. No.: WO97/25303

PCT Pub. Date: Jul. 17, 1997

[30] Foreign Application Priority Data

Jan. 4, 1996 [GB] United Kingdom .................. 9600072

[51] Int. Cl.$^6$ ...................................................... C07C 41/00
[52] U.S. Cl. ............................................................ 568/683
[58] Field of Search ............................................... 568/683

[56] References Cited

U.S. PATENT DOCUMENTS 5,750,807  5/1998  Burgess ................................. 570/142

*Primary Examiner*—Michael L. Shippen

[57] ABSTRACT

Process for producing Sevoflurane anaesthetic which comprises reacting hexafluoroisopropyl alcohol with essentially pure bis(fluoromethyl)ether. The bis(fluoromethyl)ether is preferably obtained by the reaction of formaldehyde with hydrogen fluoride.

5 Claims, No Drawings

PROCESS FOR THE PRODUCTION OF FLUOROMETHYLHEXAFLUOROISO-PROPYLETHER

This invention relates to a process for the production of fluoromethylhexafluoroisopropylether of formula $CH_2F.CH(CF_3)_2$ which is the anaesthetic "Sevoflurane".

Several processes have been proposed for the production of Sevoflurane including the reaction of hexafluoroisopropyl alcohol, $(CF_3)_2CHOH$, with formaldehyde and hydrogen fluoride. One such process comprising adding hexafluoroisopropyl alcohol to a mixture of paraformaldehyde and hydrogen fluoride plus sufficient sulphuric acid to sequester most of the water formed at a temperature above 57° C. is described in U.S. Pat. No. 4,250,334. A similar process comprising mixing hexafluoroisopropyl alcohol, formaldehyde, hydrogen fluoride and a dehydrating agent such as sulphuric acid is described in U.S. Pat. No. 4,469,898.

A process for producing an alpha-fluoroether such as and including Sevoflurane is described in International Patent Publication No WO 93/12057, the process comprising reacting a non-enolisable aldehyde such as formaldehyde with hydrogen fluoride to form an intermediate and reacting the intermediate with an alcohol such as hexafluoroisopropyl alcohol to form an alpha-fluoroether such as Sevofluorane. The production of Sevoflurane by adding hexafluoroisopropyl alcohol to the reaction mixture derived from trioxane (as the source of formaldehyde) and hydrogen fluoride and containing the intermediate bis(fluoromethyl)ether is described in Example 19.

As is described in WO 93/12057, the reaction products obtained in Example 19 comprised mainly unreacted hexafluoroisopropyl alcohol (72% by mass spectroscopic analysis) and unreacted bis(fluoromethyl)ether (22%) and the yield of Sevoflurane was only 4.9%. This very low yield of Sevoflurane renders the process unsuitable or at best barely suitable for industrial application even with recovery anti recycle of unreacted hexafluoroisopropyl alcohol and bis(fluoromethyl)ether.

The present invention is based on the discovery that separation of the intermediate bis(fluoromethyl)ether from the reaction mixture before addition of the hexafluoroisopropyl alcohol results in a process in which Sevoflurane is obtained in high yield and in particular can be obtained as the major product of the reaction.

According to the present invention there is provided a process for the production of fluoromethylhexafluoroisopropylether [Sevoflurane] which comprises reacting essentially pure bis(fluoromethyl) ether with hexafluoroisopropyl alcohol and recovering the resulting fluoromethylhexafluoroisopropylether from the reaction products.

The bis(fluoromethyl)ether is conveniently and preferably produced by the reaction of formaldehyde or a source of formaldehyde with hydrogen fluoride and according to a particular embodiment of the invention there is provided a process for the production of fluoromethylhexafluoroisopropylether which comprises reacting formaldehyde with hydrogen fluoride to produce a reaction mixture containing bis(fluoromethyl)ether, separating essentially pure bis(fluoromethyl)ether from the reaction mixture, reacting the resulting essentially pure bis(fluoromethyl)ether with hexafluoroisopropyl alcohol and recovering the resulting fluoromethylhexafluoroisopropylether from the reaction products.

The reaction between the bis(fluoromethyl)ether and the hexafluoroisopropyl alcohol is conveniently carried out at ambient temperature, say 20° C. to 30° C. and at atmospheric pressure, although if desired subatmospheric or superatmospheric pressure and a range of temperatures from about 0° C. to about 100° C. may be employed. The reaction is preferably carried out in the presence of an acid such as sulphuric acid. A slight exotherm resulting in a rise in temperature of the reaction mixture may be observed but in general there is no real advantage in applying heat to the reaction mixture.

The reaction can be readily carried out to result in complete conversion of the hexafluoroisopropyl alcohol and with an acceptable selectivity to the desired Sevoflurane product although a significant amount, say 20% or more, of the acetal $(CF_3)_2CHOCH_2OCH_2F$ is usually produced as a by-product. It is a matter of mere routine experimentation to optimise the reaction conditions to maximise the yield of Sevoflurane and minimise the yield of by-products such as the metal. A reaction product mixture in which Sevoflurane is the major component with a yield of at least about 55% and preferably about 60% or more is obtained. Carrying out the reaction with complete conversion of the hexafluoroisopropyl alcohol obviates the need to recover and recycle unreacted alcohol.

The amounts of bis(fluoromethyl)ether and hexafluoroisopropyl alcohol will usually be such that the molar ratio of the ether to the alcohol is from about 0.5:1 to about 1.5:1. In general about equimolar amounts of ether and alcohol or an excess of the ether will be used to ensure complete conversion of the alcohol. However, it has been observed that a large excess of the ether is undesirable in that it tends to result in the formation of a precipitate of granular crystals (possibly due to polymerisation of products of decomposition of the ether) and we prefer to employ a mole ratio of ether to alcohol of no greater than about 2:1.

The separation, recovery and purification of Sevoflurane from product streams containing it is known and any of the known methods may be used in the process of the invention. Such methods will usually include at least one distillation step and will usually include a step of separating and recovering any bis(fluoromethyl)ether present in the product stream. The ether recovered from the product stream can be recycled to the reaction with hexafluoroisopropyl alcohol.

The process can be operated as a batch or continuous process or a combination thereof but is preferably operated as a continuous process with recycle of recovered bis(fluoromethyl)ether.

As stated herinbefore, a prefered embodiment of the invention includes the step of producing the bis(fluoromethyl)ether by reaction of formaldehyde (or a polymeric form of formaldehyde such as paraformaldehyde or trioxane) with hydrogen fluoride. Any of the known methods for production of the bis(fluoromethyl)ether may be employed as the ether formation step of this embodiment of the present invention. The production of bis(fluoromethyl) ether from formaldehyde and hydrogen fluoride is described, for example, in European Patent Publication No. 518,506 and in International Patent Publications No. WO 93/10070, WO 93/12057 and WO 93/22265, the disclosures of which are incorporated herein by reference. In the present invention we especially prefer to employ the ether production process described in International Patent Publication No. WO 93/10070 which comprises reacting formaldehyde with hydrogen fluoride in a reaction-distillation column from which the ether is withdrawn in essentially pure form and in particular essentially free from water.

The invention is illustrated but in no way limited by the following Example.

EXAMPLE.

Bis(fluoromethyl)ether (2 g) of purity approximately 99% was mixed with stirring into hexafluoroisopropyl alcohol (4.1 g) at room temperature (approximately 25° C.) and pressure and sulphuric acid (1 ml of 98% acid) was added to the mixture. A slight exotherm was noted. After 10 minutes, the mixture was neutralised by adding sodium hydroxide and then analysed by gas chromatography/mass spectometry.

The composition of the product mixture determined by GC/MS analysis was:

|  | % age of mixture |
|---|---|
| Sevoflurane | 59.7 |
| Acetal* | 21.6 |
| Bis(fluoromethyl)ether | 17.1 |
| Methyl formate | 1.6 |
|  | 100 |

For purposes of comparison the product mixture obtained in Example 19 of WO 93/12057 was determined by GC/MS analysis to be:

|  | % age of mixture |
|---|---|
| Sevoflurane | 4.9 |
| Acetal* | 1.3 |
| Bis(fluoromethyl)ether | 22.2 |
| Hexafluoroisopropanol | 71.6 |

We claim:

1. A process for the production of fluoromethylhexafluoroisopropylether which comprises reacting essentially pure bis(fluoromethyl)ether with hexafluoroisopropyl alcohol and recovering the resulting fluoromethylhexafluoroisopropylether from the reaction products.

2. A process as claimed in claim 1 which comprises reacting formaldehyde with hydrogen fluoride to produce a reaction mixture containing bis(fluoromethyl)ether, separating essentially pure bis(fluoromethyl)ether from the reaction mixture and reacting the essentially pure bis(fluoromethyl)ether with hexafluoroisopropyl alcohol.

3. A process as claimed in claims 1 in which the essentially pure bis(fluoromethyl)ether is reacted with hexafluoroisopropyl alcohol in the presence of an acid.

4. A process as claimed in claim 1 in which the molar ratio of bis(fluoromethyl)ether to hexafluoroisopropyl alcohol is 0.5:1 to 2:1.

5. A process as claimed in claim 1 in which the yield of fluoromethyl(hexafluoromethylhexafluoroisopropylether is at least about 55%.

* * * * *